(12) United States Patent
Yan et al.

(10) Patent No.: US 9,775,583 B2
(45) Date of Patent: Oct. 3, 2017

(54) METHOD AND DEVICE FOR POSITIONING A DOPPLER ULTRASOUND TRANSDUCER FOR BLOOD FLOW MEASUREMENT AND A SYSTEM FOR BLOOD FLOW MEASUREMENT

(75) Inventors: Ming Yan, Shanghai (CN); Yinan Chen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 903 days.

(21) Appl. No.: 14/000,632

(22) PCT Filed: Feb. 27, 2012

(86) PCT No.: PCT/IB2012/050897
§ 371 (c)(1),
(2), (4) Date: Aug. 21, 2013

(87) PCT Pub. No.: WO2012/117337
PCT Pub. Date: Sep. 7, 2012

(65) Prior Publication Data
US 2013/0331702 A1  Dec. 12, 2013

(30) Foreign Application Priority Data
Mar. 1, 2011  (WO) ................ PCT/CN2011/071423

(51) Int. Cl.
*A61B 8/06* (2006.01)
*A61B 5/022* (2006.01)
(Continued)

(52) U.S. Cl.
CPC ............... *A61B 8/06* (2013.01); *A61B 5/022* (2013.01); *A61B 8/42* (2013.01); *A61B 8/488* (2013.01); *A61B 8/08* (2013.01); *A61B 8/0891* (2013.01)

(58) Field of Classification Search
CPC .................................. A61B 5/022; A61B 8/06
See application file for complete search history.

(56) References Cited

U.S. PATENT DOCUMENTS 5,669,388 A    9/1997  Vilkomerson
6,471,655 B1 * 10/2002  Baura ................ A61B 5/02028
                                                      600/485
(Continued)

FOREIGN PATENT DOCUMENTS

WO         0100087 A1    1/2001
WO       2009125349 A2  10/2009

*Primary Examiner* — Joseph M Santos Rodriguez

(57) ABSTRACT

The method of positioning a Doppler ultrasound transducer for performing blood flow measurement according to the invention comprises the steps of: detecting a pressure oscillation signal from an inflated cuff placed on patient's artery; detecting an ultrasound pulse signal from the Doppler ultrasound transducer placed along the artery; deriving a first signal from the pressure oscillation signal and the ultrasound pulse signal, the first signal indicating the degree of synchronization between the pressure oscillation signal and the ultrasound pulse signal; and outputting an indication signal to indicate the Doppler ultrasound transducer is in a desired position when the first signal satisfies a predefined condition. Since the synchronization property of the cuff pressure oscillation signal and the ultrasound signal caused by the blood flow is utilized to determine whether the transducer is well positioned or not, ultrasound signal, which is a pulse signal but not reflecting the blood flow of the artery, could be determined as not in synchronization with the oscillation signal and therefore the accuracy of the positioning could be improved.

18 Claims, 3 Drawing Sheets

(51) Int. Cl.
    *A61B 8/00*    (2006.01)
    *A61B 8/08*    (2006.01)

(56) References Cited

U.S. PATENT DOCUMENTS

2008/0119741 A1    5/2008  Friedman et al.
2008/0119743 A1    5/2008  Friedman et al.
2010/0056930 A1    3/2010  Flaherty et al.

* cited by examiner

METHOD AND DEVICE FOR POSITIONING A DOPPLER ULTRASOUND TRANSDUCER FOR BLOOD FLOW MEASUREMENT AND A SYSTEM FOR BLOOD FLOW MEASUREMENT

FIELD OF THE INVENTION

The invention relates to Doppler ultrasound, particularly to a method and device for positioning a Doppler ultrasound transducer for blood flow measurement and a system for blood flow measurement.

BACKGROUND OF THE INVENTION

Doppler ultrasound is widely used to measure the blood flow velocity in clinical applications. FIG. 1 shows the working principle of Doppler ultrasound for measuring blood flow. To perform a blood pressure measurement, a cuff is provided around the patient's arm and an air bag in the cuff is inflated to increase the pressure in the cuff. When the pressure is increased to a predefined level (higher than the systolic pressure), the artery is blocked and then the air bag is deflated slowly. When the pressure in the air bag is equal to the systolic pressure, the artery is opened and the blood flow is restored. When a Doppler ultrasound 11 is applied to monitor the deflation procedure, it will detect a signal when the artery is open. The corresponding pressure in the cuff at this moment is the systolic pressure. The Doppler ultrasound is used as the golden standard method to measure the systolic pressure.

However, as shown in FIG. 1, the Doppler ultrasound 11 sends a Doppler ultrasound signal 12 towards the blood flow 15 in an artery 14 and the signal is limited to a small scope. If the artery is not in the scope, the Doppler ultrasound cannot measure the reflected signal 13. Therefore, the position of the Doppler ultrasound transducer should be adjusted so as to be placed on the artery, so that it can acquire a good SNR to clearly detect the reflected Doppler ultrasound signal of the blood flow. Further, this position should be maintained during the measurement procedure.

In order to make sure that the Doppler ultrasound transducer is well placed, the conventional procedure to position the transducer needs an operator's judgment, for example, a doctor or physician, according to his/her experience.

Specifically, the operator places the transducer on the brachial or ankle of a patient, such that it can be approximately above the artery. After this step, the operator may listen to the audio output of the Doppler ultrasound, and according to his/her experience, if a clear and regular sound output, which reflects the blood flow of the artery, can be heard, the operator judges that the transducer is well placed. Otherwise, the position of the transducer should be adjusted until a clear and regular sound can be heard.

Since the above procedure to position the transducer needs an operator's judgment, based on the audio output of the Doppler ultrasound, it is not automatic and thus not very convenient. Furthermore, in the ABI measurement, ultrasound signals on four limbs will be measured, thus the audio outputs will interfere with each other during the transducer positioning procedure and it becomes more difficult for the operator to judge whether the transducer is well placed.

In addition to the conventional procedure to position the transducer, it could readily occur to those skilled in the art to use a processing unit to process the Doppler ultrasound signal in order to determine whether the signal is a pulse signal.

However, although the signal may be a pulse signal, it may not necessarily reflect the blood flow of the artery. For example, the pulse signal may be caused by the flapping of the muscle near the transducer.

Therefore, on the one hand, to determine whether the transducer is well placed by simply determining whether the Doppler ultrasound signal is a pulse signal may not be accurate enough and may cause some mistakes.

On the other hand, to make this positioning procedure accurate, when the Doppler ultrasound signal detected is determined to be a pulse signal, the ultrasound pulse signal should be applied using a complicated algorithm and processing to determine that the pulse signal actually is the signal reflecting the blood flow of the artery.

SUMMARY OF THE INVENTION

The present invention is based on the insight that to make sure that a pulse signal detected from the Doppler ultrasound is the signal reflecting the blood flow of the artery, a reference could be adopted.

Specifically, the inventor has found that the cuff pressure oscillation signal synchronizes with the ultrasound pulse signal caused by the blood flow. The basis behind this observation is the property of the pulse waves. Following the heart contractions, the pulse wave of the blood flow will propagate down the artery. The pulse wave will generate the oscillation signal in the cuff and also cause an increase of the speed of the blood flow in the artery. Because the Doppler ultrasound signal will increase with the blood flow speed, a pulse signal can be observed. Since the pressure oscillation signal and the ultrasound pulse signal are related to the same pulse wave signal, the oscillation signal and ultrasound signal should be synchronized.

The present invention provides a method and a device for positioning a Doppler ultrasound transducer for blood flow measurement to fulfill the above concept.

According to one aspect of the present invention, there is provided a method of positioning a Doppler ultrasound transducer for blood flow measurement, comprising the steps of:

detecting a pressure oscillation signal from an inflated cuff placed on an artery of a patient;

detecting an ultrasound pulse signal from the Doppler ultrasound transducer placed along the artery;

deriving a first signal from the pressure oscillation signal and the ultrasound pulse signal, the first signal indicating the degree of synchronization between the pressure oscillation signal and the ultrasound pulse signal; and outputting an indication signal to indicate that the Doppler ultrasound transducer is in a desired position when the first signal satisfies a predefined condition.

With the method of the present invention, the operator does not have to listen to the audio output of the ultrasound signal any more and therefore the positioning procedure can be performed automatically, thereby reducing the involvement of the operator as much as possible.

Further, since the synchronization property of the cuff pressure oscillation signal and the ultrasound signal caused by the blood flow is utilized to determine whether the transducer is well positioned or not, the ultrasound signal, which is a pulse signal but which does not reflect the blood flow of the artery, could be found to be not in synchronization with the pressure oscillation signal, and thus the positioning accuracy could be improved.

In an embodiment of the present invention, the first signal is derived from the time intervals measured between two consecutive peaks of the pressure oscillation signal $\Delta t_{osi}$ (i=1 ... n) and the time intervals measured between two corresponding consecutive pulses of the ultrasound pulse signal $\Delta t_{usi}$ (i=1 ... n).

In a further embodiment, the first signal is derived by computing $(\Delta t_{usi} - \Delta t_{osi})/\Delta t_{osi}$, and the first signal satisfies the predefined condition if $(\Delta t_{usi} - \Delta t_{osi})/\Delta t_{osi} \leq 8\%$, wherein n is at least two.

According to the study of the inventor, although in theory the difference between the time intervals measured above should be zero if these two signals synchronize with each other, the difference between the time intervals is usually approximately zero due to the commonly known error in measurement and the time delay. With the above criterion for computing the first signal and the predefined condition, the first signal indicated above could indicate the degree of synchronization between the pressure oscillation signal and the ultrasound pulse signal, and the predefined condition is selected to be 8% accordingly to improve the accuracy with respect to determination of synchronization.

In a preferred embodiment, n is five, so that the positioning accuracy of the transducer could be substantially improved.

In an embodiment, the step of detecting a pressure oscillation signal from the inflated cuff placed on an artery of a patient comprises processing a pressure signal obtained by a pressure sensor connected with the inflated cuff to determine whether the pressure oscillation signal is detected, and increasing the pressure in the inflated cuff if the pressure oscillation signal is not detected.

In a further embodiment, the pressure in the inflated cuff is increased to about 80 mmHg to ensure that a pressure oscillation signal from the cuff could be measured.

In an embodiment, the step of detecting an ultrasound pulse signal from the Doppler ultrasound transducer placed along the artery comprises determining whether the ultrasound signal from the Doppler ultrasound transducer placed along the artery is a pulse signal if the pressure oscillation signal is detected.

In a further embodiment, the method further comprises the step of outputting a prompting signal prompting the operator to relocate the Doppler ultrasound transducer if the ultrasound signal from the Doppler ultrasound transducer placed along the artery is not a pulse signal.

In an embodiment, the step of outputting the indication signal comprises turning on an indication lamp of the Doppler ultrasound transducer or changing the color of the Doppler ultrasound transducer on the display screen of the Doppler ultrasound device.

In an embodiment of the invention, the method further comprises a step of outputting a prompting signal prompting the operator to relocate the Doppler ultrasound transducer if the first signal does not satisfy the predefined condition.

Other objects and results of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, in which.

The same reference signs in the figures indicate similar or corresponding features and/or functionalities.

DETAILED DESCRIPTION

An embodiment of the present invention will be described hereinafter in more detail with reference to the drawings.

Figure 1:
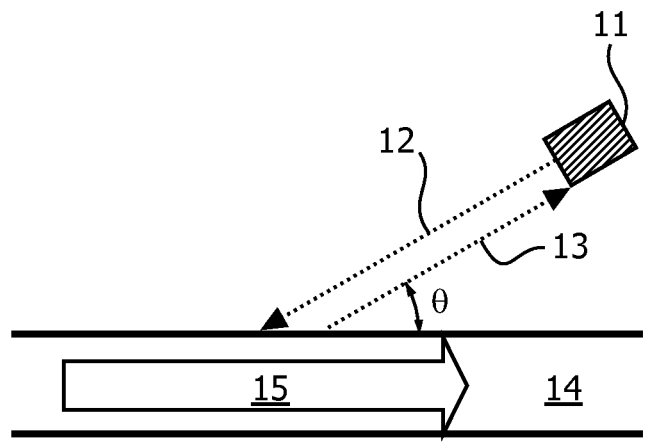
FIG. 1 shows the principle of Doppler ultrasound for blood flow.
Figure 2:
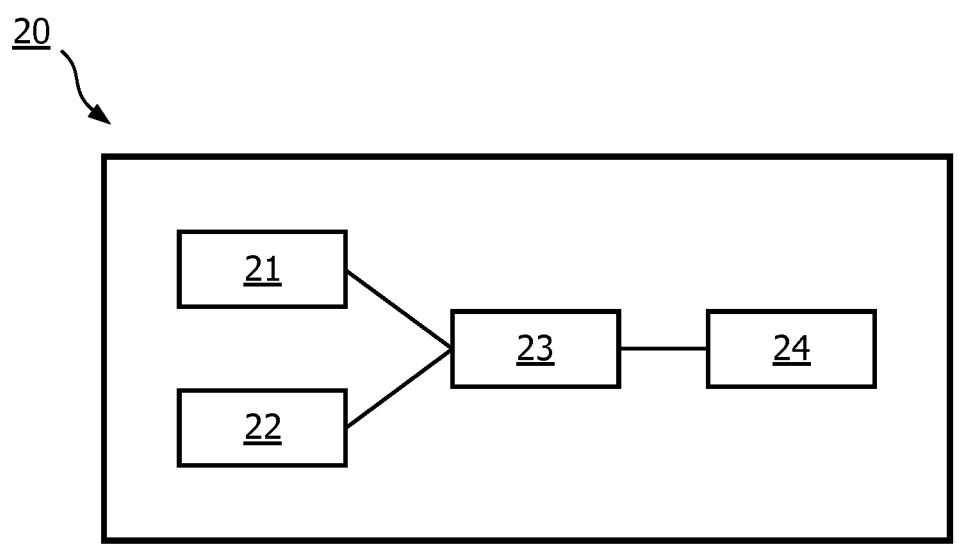
FIG. 2 is a block diagram of the device for positioning a Doppler ultrasound transducer for blood flow measurement according to an embodiment of the present invention.

FIG. 2 is a block diagram of the device 20 for positioning a Doppler ultrasound transducer for blood flow measurement according to an embodiment of the present invention.

Referring to FIG. 2, the device 20 comprises a first detector 21 for detecting a pressure oscillation signal from an inflated cuff placed on an artery of a patient.

In an embodiment, the first detector 21 processes a pressure signal obtained by a pressure sensor connected with the inflated cuff to determine whether the pressure oscillation signal is detected, and the operator will increase the pressure in the inflated cuff if the pressure oscillation signal is not detected.

In operation, the cuff is first inflated to a proper pressure, which does not have to be a high pressure to occlude the artery. The pressure is acceptable as long as the pressure oscillation signal can be detected. Actually, if the pressure is appropriate and the cuff is well positioned above the artery, an oscillation signal will be generated in the cuff due to the pulse wave of the blood flow of the artery.

In practice, the pressure in the airbag of the cuff is increased to about 80 mmHg.

The device 20 further comprises a second detector 22 for detecting an ultrasound pulse signal from the Doppler ultrasound transducer placed along the artery.

In this embodiment, the second detector 22 determines directly whether the ultrasound signal from the Doppler ultrasound transducer placed along the artery is a pulse signal without the determination result of the first detector 21.

However, as is easily understood by those skilled in the art, in another embodiment, the second detector 22 may determine whether the ultrasound signal from the Doppler ultrasound transducer placed along the artery is a pulse signal only when a pressure oscillation signal is detected by the first detector 21.

In practice, if the transducer is not well positioned, the ultrasound signal from the Doppler ultrasound transducer may be very weak or may not be a pulse signal. In that case, an ultrasound pulse signal cannot be detected by the second detector 22 and it means that the transducer is not well positioned.

If the ultrasound signal from the Doppler ultrasound transducer placed along the artery is not a pulse signal, a prompting signal prompting the operator to relocate the Doppler ultrasound transducer may be outputted.

The device 20 further comprises a processor 23 for deriving a first signal from the pressure oscillation signal and the ultrasound pulse signal, the first signal indicating the degree of synchronization between the pressure oscillation signal and the ultrasound pulse signal.

As mentioned above, if an ultrasound pulse signal detected from the Doppler ultrasound is the signal reflecting the blood flow of the artery, then, taking into account that the pressure oscillation signal and the ultrasound pulse signal relate to the same pulse wave signal of the blood flow of the artery, these two signals should synchronize with each other.

In practice, if the transducer is not well positioned, even if the ultrasound signal is a pulse signal, it does not synchronize with the pressure oscillation signal and therefore the pulse signal detected from the Doppler ultrasound is not the signal reflecting the blood flow of the artery but something else. In that case, the first signal derived from the processor 23 will indicate that these two signals do not synchronize with each other, which means that the transducer is not well positioned.

As for how to derive the first signal indicating the degree of synchronization between the pressure oscillation signal and the ultrasound pulse signal, it will be clear to those skilled in the art that many techniques in signal processing may be used. Details will be further elaborated in the following with reference to FIG. 3.

Device 20 further comprises an interface 24 for outputting an indication signal to indicate that the Doppler ultrasound transducer is in a desired position when the first signal satisfies a predefined condition.

In practice, the indication signal may take many forms.

For example, the indication signal may be outputted by the interface 24 turning on an indication lamp of the Doppler ultrasound transducer or changing the color of the Doppler ultrasound transducer on the display screen of the Doppler ultrasound device.

In a further embodiment of the invention, if the first signal does not satisfy the predefined condition, the interface 24 will also output a prompting signal prompting the operator to relocate the Doppler ultrasound transducer.

In a further embodiment of the invention, as mentioned above, if the ultrasound signal from the Doppler ultrasound transducer placed along the artery is not a pulse signal, the interface 24 may output a prompting signal prompting the operator to relocate the Doppler ultrasound transducer.

Figure 3:
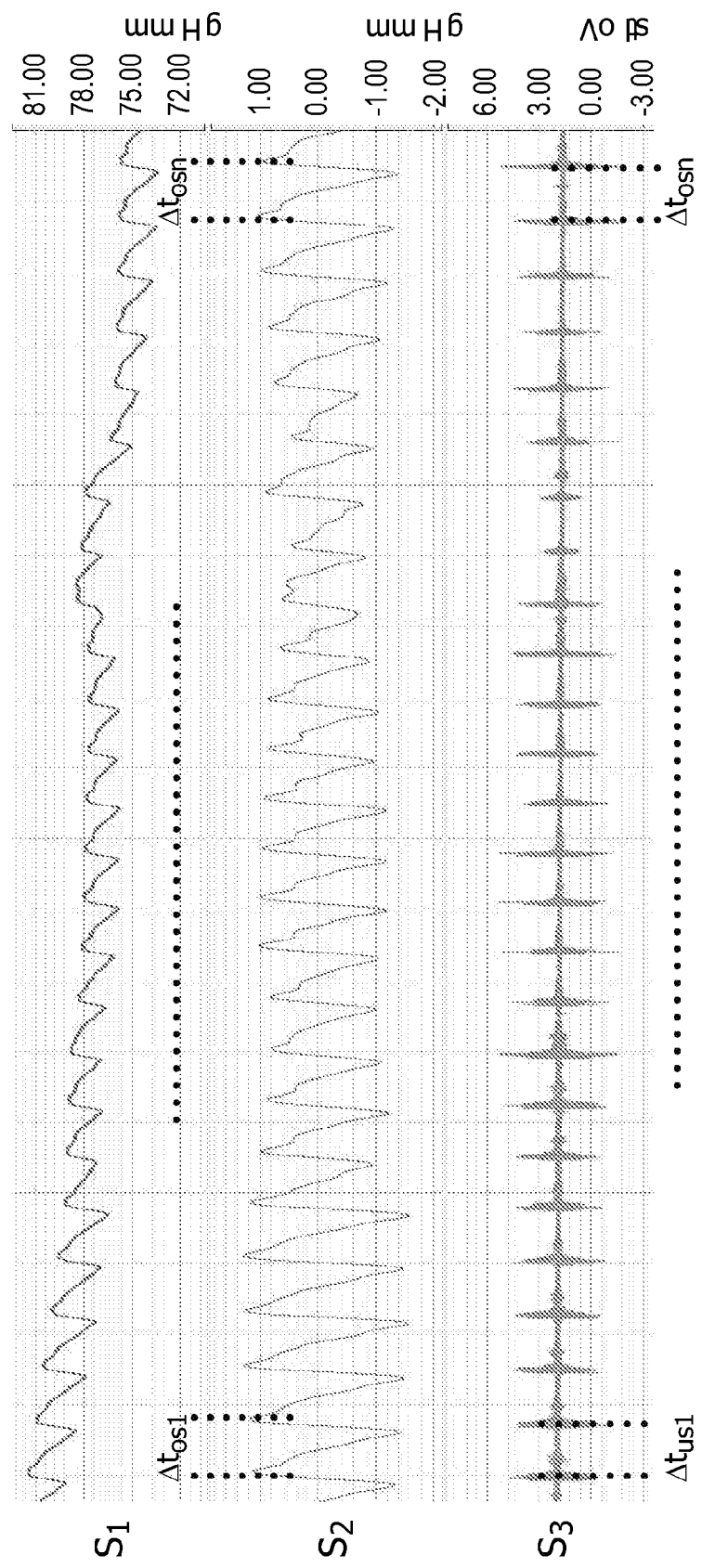
FIG. 3 shows the synchronization characteristic between the oscillation signal and the ultrasound signal.

FIG. 3 shows the synchronization characteristic between the oscillation signal and the ultrasound signal.

As shown in FIG. 3, the top graph represents the cuff pressure $S_1$ and it can be seen that there is slight time difference between the detected oscillation signal $S_2$ and the Doppler ultrasound signal $S_3$. The time difference is caused by the distance between the cuff and the transducer and also the blood flow speed. Sometimes, when the transducer is positioned far from the cuff, there will be a delay between these two signals. However, when the cuff position and the transducer position are fixed, the time difference is quite stable.

In view of this, in an embodiment in accordance with the present invention, the processor 23 derives the first signal in accordance with the time difference between the time intervals of the two signals, since it should be fairly small if the two signals synchronize.

In an embodiment in accordance with the present invention, the first signal is derived from the time intervals measured between two consecutive peaks of the pressure oscillation signal $\Delta t_{osi}$ (i=1 . . . n) and the time intervals measured between two corresponding consecutive pulses of the ultrasound pulse signal $\Delta t_{usi}$ (i=1 . . . n).

In a further embodiment, the first signal is derived by computing $(\Delta t_{usi} - \Delta t_{osi})/\Delta t_{osi}$, and it is determined that the pulse signal synchronizes with the oscillation signal if the time intervals measured between two consecutive peaks of the oscillation signal $\Delta t_{osi}$ (i=1 . . . n) and the time intervals measured between two corresponding consecutive pulses of the ultrasound signal $\Delta t_{usi}$ (i=1 . . . n) satisfy the following:

$(\Delta t_{usi} - \Delta t_{osi})/\Delta t_{osi} \leq 8\%$, wherein n is at least two.

In other words, if the first signal satisfies the above predefined condition, it is determined that the two signals synchronize, and the interface 24 outputs an indication signal to indicate that the Doppler ultrasound transducer is in a desired position.

In a preferred embodiment, n could be five or even more in order to avoid error of determination and hence improve the positioning accuracy.

As discussed above, according to the present invention, the operator does not have to listen to the audio output of the ultrasound signal any more and therefore the positioning procedure can be done automatically, thereby reducing the involvement of the operator as much as possible.

Further, since the synchronization property of the cuff pressure oscillation signal and the ultrasound signal caused by the blood flow is utilized to determine whether the transducer is well positioned or not, the ultrasound signal, which is a pulse signal but which does not reflect the blood flow of the artery, could be determined to be not in synchronization with the pressure oscillation signal and therefore the accuracy of the positioning could be improved.

Figure 4:
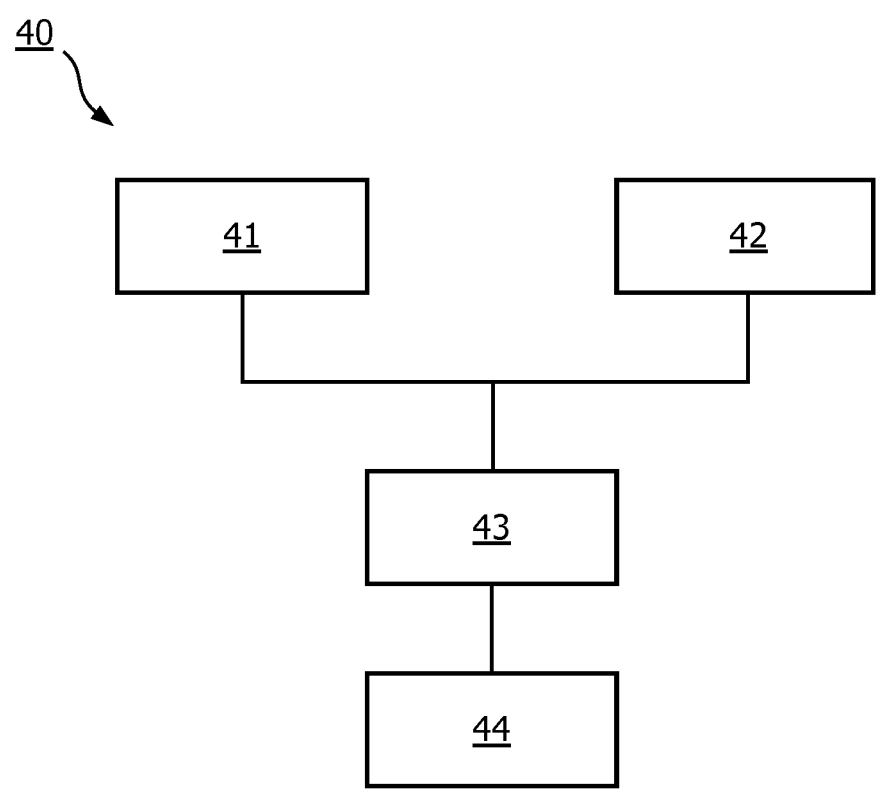
FIG. 4 shows a flowchart of the method of positioning a Doppler ultrasound transducer for blood flow measurement according to an embodiment of the present invention.

FIG. 4 shows a flowchart of the method 40 of positioning a Doppler ultrasound transducer for blood flow measurement according to an embodiment of the present invention.

As shown in FIG. 4, the method 40 according to the present invention comprises a detecting step 41 of detecting a pressure oscillation signal from an inflated cuff placed on an artery of a patient. The function of step 41 can be executed by the first detector 21.

The method further comprises a detecting step 42 of detecting an ultrasound pulse signal from the Doppler ultrasound transducer placed along the artery. The function of step 42 can be executed by the second detector 22.

The method further comprises a deriving step 43 of deriving a first signal from the pressure oscillation signal and the ultrasound pulse signal, the first signal indicating the degree of synchronization between the pressure oscillation signal and the ultrasound pulse signal. The function of step 43 can be executed by the processor 23.

The method further comprises an outputting step 44 of outputting an indication signal to indicate that the Doppler ultrasound transducer is in a desired position when the first signal satisfies a predefined condition. The function of step 44 can be executed by the interface 24.

In an embodiment, the detecting step 41 of detecting a pressure oscillation signal from the inflated cuff placed on an artery of a patient comprises processing a pressure signal obtained by a pressure sensor connected with the inflated cuff to determine whether the pressure oscillation signal is detected, and increasing the pressure in the inflated cuff if the pressure oscillation signal is not detected.

In a preferred embodiment, the pressure in the inflated cuff is increased to about 80 mmHg.

In an embodiment, the detecting step 42 of detecting an ultrasound pulse signal from the Doppler ultrasound transducer placed along the artery comprises determining whether the ultrasound signal from the Doppler ultrasound transducer placed along the artery is a pulse signal if the pressure oscillation signal is detected. If the ultrasound signal from the Doppler ultrasound transducer placed along the artery is not a pulse signal, a prompting signal prompting the operator to relocate the Doppler ultrasound transducer will be outputted.

In an embodiment, in the deriving step 43, as described above in conjunction with FIG. 3, the first signal is derived from the time intervals measured between two consecutive peaks of the pressure oscillation signal $\Delta t_{osi}$ (i=1 . . . n) and the time intervals measured between two corresponding consecutive pulses of the ultrasound pulse signal $\Delta t_{usi}$ (i=1 . . . n).

In a further embodiment, the first signal is derived by computing $(\Delta t_{usi} - \Delta t_{osi})/\Delta t_{osi}$ and it is determined that the pulse signal synchronizes with the oscillation signal if the time intervals measured between two consecutive peaks of the oscillation signal $\Delta t_{osi}$ (i=1 . . . n) and the time intervals measured between two corresponding consecutive pulses of the ultrasound signal $\Delta t_{usi}$ (i=1 . . . n) satisfy the following:
$(\Delta t_{usi} - \Delta t_{osi})/\Delta t_{osi} \leq 8\%$, wherein n is at least two.

In other words, if the first signal satisfies the above predefined condition, it is determined that the two signals synchronize with each other and an indication signal will be outputted to indicate that the Doppler ultrasound transducer is in a desired position.

In a preferred embodiment, n could be five or even more in order to avoid error of determination and hence improve the accuracy of the positioning.

In an embodiment, the outputting step 44 of outputting the indication signal comprises turning on an indication lamp of the Doppler ultrasound transducer or changing the color of the Doppler ultrasound transducer on the display screen of the Doppler ultrasound device.

In a further embodiment of the invention, the method further comprises outputting a prompting signal prompting the operator to relocate the Doppler ultrasound transducer if the first signal does not satisfy the predefined condition.

As is easily understood by those skilled in the art, the above described method and device for positioning a Doppler ultrasound transducer can be used in a system for blood flow measurement, which comprises a cuff placed on an artery of a patient, a Doppler ultrasound transducer placed along the artery, and the device (20) for positioning a Doppler ultrasound transducer for blood flow measurement according to the present invention.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The use of the words first, second and third, et cetera, does not indicate any ordering. These words are to be interpreted as names.

The invention claimed is:

1. A method of positioning a Doppler ultrasound transducer for blood flow measurement, comprising:
    with a pressure sensor, detecting a pressure oscillation from an inflated cuff placed on an artery of a patient and outputting a pressure oscillation signal;
    with a Doppler ultrasound transducer placed along the artery, detecting an ultrasound pulse and outputting an ultrasound pulse signal;
    with at least one electronic processor, deriving, from the pressure oscillation signal and the ultrasound pulse signal, a first signal indicating the degree of synchronization between the pressure oscillation signal and the ultrasound pulse signal, the first signal being derived from the time intervals measured between two consecutive peaks of the pressure oscillation signal $\Delta t_{osi}$ (i=1 . . . n) and the time intervals measured between two corresponding consecutive pulses of the ultrasound pulse signal $\Delta t_{usi}$ (i=1 . . . n); and
    on a display, indicating that the Doppler ultrasound transducer is in a desired position in response to the first signal satisfying a predefined condition including $(\Delta t_{usi} - \Delta t_{osi})/\Delta t_{osi} \leq x\ \%$, wherein n is at least two and x is a preselected percent.

2. The method of claim 1, wherein the at least one electronic processor is programmed to:
    derive the first signal by computing $(\Delta t_{usi} - \Delta t_{osi})/\Delta t_{osi}$, and the first signal satisfies the predefined condition in response to $(\Delta t_{usi} - \Delta t_{osi})/\Delta t_{osi} \leq 8\%$.

3. The method of claim 2, wherein n is five.

4. The method of claim 1, wherein detecting a pressure oscillation signal from the inflated cuff placed on an artery of a patient comprises, with the at least one electronic processor:
    obtaining the pressure signal from the pressure sensor connected with the inflated cuff;
    determine whether the pressure oscillation signal is detected by the Doppler ultrasound transducer; and
    increasing the pressure in the inflated cuff in response to the pressure oscillation signal not being detected.

5. The method of claim 4, inflating the cuff to about 80 mmHg.

6. The method of claim 4, wherein detecting the ultrasound pulse signal from the Doppler ultrasound transducer placed along the artery comprises:
    determining, with the Doppler ultrasound transducer, the pulse and outputting the ultrasound pulse signal in response to the pressure oscillation signal being detected.

7. The method of claim 6, further comprising:
    with the at least one electronic processor, outputting a prompting signal to the display prompting the operator to relocate the Doppler ultrasound transducer in response to the ultrasound signal from the Doppler ultrasound transducer is not a pulse.

8. The method of claim 1, wherein outputting the indication signal comprises:
    turning on an indication lamp of the Doppler ultrasound transducer or changing the color of the Doppler ultrasound transducer on the display of the Doppler ultrasound device.

9. A device for positioning a Doppler ultrasound transducer for blood flow measurement, comprising:
    at least one electronic processor programmed to:
        receive a pressure oscillation signal from an inflated cuff placed on an artery of a patient;
        receive an ultrasound pulse signal from a Doppler ultrasound transducer placed along the artery;
        derive a first signal from the pressure oscillation signal and the ultrasound pulse signal, the first signal indicating the degree of synchronization between the pressure oscillation signal and the ultrasound pulse signal, the first signal being derived by from the time intervals measured between two consecutive peaks of the pressure oscillation signal $\Delta t_{osi}$(i=1 . . . n) and the time intervals measured between two corresponding consecutive pulses of the ultrasound pulse signal $\Delta t_{usi}$(i=1 . . . n); and an interface configured to output an indication signal to indicate that the Doppler ultrasound transducer is in a desired position when the first signal satisfies a predefined condition including $(\Delta t_{usi}-\Delta t_{osi})/\Delta t_{osi} \leq x$ %, wherein n is at least two and x is a preselected percent.

10. The device according to claim 9, wherein the at least one electronic processor is programmed to:
derive the first signal by computing $(\Delta t_{usi}-\Delta t_{osi})/\Delta t_{osi}$, and the first signal satisfies the predefined condition in response to $(\Delta t_{usi}-\Delta t_{osi})/\Delta t_{osi} \leq 8\%$.

11. The device according to claim 9, further including a pressure sensor connected with the inflated cuff to sense the pressure oscillations and output a pressure oscillation signal;
wherein the at least one electronic processor is further reprogramed to:
determine whether the pressure oscillation signal is detected; and
increase the pressure in the inflated cuff in response to the pressure oscillation signal not being detected.

12. The device according to claim 11, wherein the at least one electronic processor is programmed to:
determine whether the ultrasound signal from the Doppler ultrasound transducer placed along the artery is a pulse signal in response to the pressure oscillation signal being detected.

13. A system for blood flow measurement, comprising
a cuff placed on an artery of a patient;
a Doppler ultrasound transducer placed along the artery; and
the device for positioning a Doppler ultrasound transducer for blood flow measurement according to claim 9.

14. The device according to claim 9, wherein the interface is configured to:
output a relocation signal to the display for relocating the Doppler ultrasound transducer when the ultrasound signal from the Doppler ultrasound transducer placed along the artery is not a pulse signal.

15. The device according to claim 14, wherein the interface is configured to at least one of:
turn on an indication lamp of the Doppler ultrasound transducer; and
change the color of the Doppler ultrasound transducer on a display of the interface.

16. A device for positioning a Doppler ultrasound transducer for blood flow measurement, the device comprising:
a cuff placed on an artery of a patient;
a pressure sensor connected with the cuff, the pressure sensor being configured to sense pressure oscillations and output a pressure oscillation signal;
a Doppler ultrasound transducer placed along an artery, the transducer being configured to sense an ultrasound pulse and output an ultrasound pulse signal;
one or more electronic processors programmed to:
receive the pressure oscillation signal from the cuff when the cuff is placed on the artery of a patient and inflated;
detect an ultrasound pulse signal from the Doppler ultrasound transducer placed along the artery;
derive a first signal from the pressure oscillation signal and the ultrasound pulse signal from the time intervals measured between two consecutive peaks of the pressure oscillation signal $\Delta t_{osi}(i=1 \ldots n)$ and the time intervals measured between two corresponding consecutive pulses of the ultrasound pulse signal $\Delta t_{usi}(i=1 \ldots n)$; and
an interface configured to:
output an indication signal to indicate that the Doppler ultrasound transducer is in a desired position when the first signal satisfies a predefined condition, the predefined condition including $(\Delta t_{usi}-\Delta t_{osi})/\Delta t_{osi} \leq x$ %, wherein n is at least two and x is a preselected percent; and
output a prompting signal to a display of the interface to relocate the Doppler ultrasound transducer when the ultrasound signal from the Doppler ultrasound transducer placed along the artery is not a pulse signal;
wherein the indication signal and the prompting signal each include one of turning on an indication lamp of the Doppler ultrasound transducer, generating a sound, or changing the color of the Doppler ultrasound transducer on the display.

17. The device according to claim 16, wherein the at least one electronic processor is further programmed to:
determine whether the pressure oscillation signal is detected; and
increase the pressure in the inflated cuff until the pressure oscillation signal is detected.

18. The device according to claim 16 wherein the at least one electronic processor is further programmed to:
in response to the pressure oscillation signal being detected, determine whether the ultrasound signal from the Doppler ultrasound transducer placed along the artery is a pulse,
wherein x is approximately 8%.

* * * * *